(12) United States Patent
Siochi

(10) Patent No.: US 6,349,129 B1
(45) Date of Patent: *Feb. 19, 2002

(54) SYSTEM AND METHOD FOR DEFINING RADIATION TREATMENT INTENSITY MAPS

(75) Inventor: Ramon Alfredo Carvalho Siochi, Apex, NC (US)

(73) Assignee: Siemens Medical Solutions USA, Inc., Iselin, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/457,601

(22) Filed: Dec. 8, 1999

(51) Int. Cl.[7] .................................................. A61N 5/10

(52) U.S. Cl. .......................................... 378/65; 378/64

(58) Field of Search ...................................... 378/65, 64

(56) References Cited

U.S. PATENT DOCUMENTS

| 5,663,999 A | 9/1997 | Siochi ......................... 378/65 |
| 5,724,403 A | 3/1998 | Siochi et al. ................ 378/150 |
| 6,134,296 A | * 10/2000 | Siochi ......................... 378/65 |

* cited by examiner

Primary Examiner—Robert H. Kim
Assistant Examiner—Courtney Thomas

(57) ABSTRACT

A method for defining an intensity map for use in delivering radiation from a radiation source to an object with a multi-leaf collimator is disclosed. The method includes defining a field on the object for radiation delivery. The field includes a plurality of cells each having a defined treatment intensity level. At least a portion of the cells are grouped to form a matrix. The method further includes modifying the treatment intensity level of the cells within the matrix such that horizontal gradients of pairs of rows of the matrix are equal to one another and vertical gradients of pairs of columns of the matrix are equal to one another. A system for defining an intensity map is also disclosed.

23 Claims, 7 Drawing Sheets

SYSTEM AND METHOD FOR DEFINING RADIATION TREATMENT INTENSITY MAPS

FIELD OF THE INVENTION

The present invention relates generally to a radiation emitting device, and more particularly, to a system and method for efficiently delivering radiation treatment.

BACKGROUND OF THE INVENTION

Radiation emitting devices are generally known and used, for instance, as radiation therapy devices for the treatment of patients. A radiation therapy device generally includes a gantry which can be swiveled around a horizontal axis of rotation in the course of a therapeutic treatment. A linear accelerator is located within the gantry for generating a high energy radiation beam for therapy. This high energy radiation beam may be an electron beam or photon (x-ray) beam, for example. During treatment, the radiation beam is trained on a zone of a patient lying in the isocenter of the gantry rotation.

In order to control the radiation emitted toward the patient, a beam shielding device, such as a plate arrangement or collimator, is typically provided in the trajectory of the radiation beam between the radiation source and the patient. An example of a plate arrangement is a set of four plates which can be used to define an opening for the radiation beam. The collimator is a beam shielding device which may include multiple leaves (e.g., relatively thin plates or rods) typically arranged as opposing leaf pairs. The plates are formed of a relatively dense and radiation impervious material and are generally independently positionable to delimit the radiation beam.

The beam shielding device defines a field on the zone of the patient for which a prescribed amount of radiation is to be delivered. The usual treatment field shape results in a three-dimensional treatment volume which includes segments of normal tissue, thereby limiting the dose that can be given to the tumor. The dose delivered to the tumor can be increased if the amount of normal tissue being irradiated is decreased and the dose delivered to the normal tissue is decreased. Avoidance of delivery of radiation to the healthy organs surrounding and overlying the tumor limits the dosage that can be delivered to the tumor.

The delivery of radiation by a radiation therapy device is typically prescribed by an oncologist. The prescription is a definition of a particular volume and level of radiation permitted to be delivered to that volume. Actual operation of the radiation equipment, however, is normally done by a therapist. The radiation emitting device is programmed to deliver the specific treatment prescribed by the oncologist. When programming the device for treatment, the therapist has to take into account the actual radiation output and has to adjust the dose delivery based on the plate arrangement opening to achieve the prescribed radiation treatment at the desired depth in the target.

The radiation therapist's challenge is to determine the best number of fields and intensity levels to optimize dose volume histograms, which define a cumulative level of radiation that is to be delivered to a specified volume. Typical optimization engines optimize the dose volume histograms by considering the oncologist's prescription, or three-dimensional specification of the dosage to be delivered. In such optimization engines, the three-dimensional volume is broken into cells, each cell defining a particular level of radiation to be administered. The outputs of the optimization engines are intensity maps, which are determined by varying the intensity at each cell in the map. The intensity maps specify a number of fields defining optimized intensity levels at each cell. The fields may be statically or dynamically modulated, such that a different accumulated dosage is received at different points in the field. Once radiation has been delivered according to the intensity map, the accumulated dosage at each cell, or dose volume histogram, should correspond to the prescription as closely as possible.

In such intensity modulation, borders between critical structures and tumor volumes are sometimes not well approximated with a standard one centimeter width leaf which provides a one centimeter by one centimeter grid (cell size) over the intensity map. A higher resolution than typically provided with the one centimeter leaf is often required. One possible solution is to provide a collimator with thinner leaves. However, the additional hardware required for the additional leaves is expensive, adds weight to the system, may reduce clearance between the treatment head and the patient, and may decrease reliability and life of the system.

Furthermore, it is also important that the final intensity map be configured such that it can be delivered with a conventional multi-leaf collimator, and that a filter process used to convert the intensity map be relatively fast so that iterations can occur quickly.

Accordingly, there is therefore, a need for a filter process for converting an intensity map into one that is ready for decomposition into an intensity map that is deliverable with a conventional multi-leaf collimator at a higher spatial resolution than is typically provided.

SUMMARY OF THE INVENTION

A method and system for defining an intensity map for use in delivering radiation from a radiation source to an object with a multi-leaf collimator are disclosed.

A method of the present invention generally includes defining a field on the object for radiation delivery. The field includes a plurality of cells each having a defined treatment intensity level. At least a portion of the cells are grouped to form a matrix. The method further includes modifying the treatment intensity level of the cells within the matrix such that horizontal gradients of pairs of rows of the matrix are equal to one another and vertical gradients of pairs of columns of the matrix are equal to one another.

A system of the present invention generally includes a processor for receiving the cells, grouping at least a portion of the cells to form a matrix, and modifying the treatment intensity level of the cells within the matrix such that horizontal gradients of pairs of rows of the matrix are equal to one another and vertical gradients of pairs of columns of the matrix are equal to one another.

The remaining cells may also be grouped into matrices and modified as required to form a deliverable intensity map for the entire field.

The above is a brief description of some deficiencies in the prior art and advantages of the present invention. Other features, advantages, and embodiments of the invention will be apparent to those skilled in the art from the following description, drawings, and claims.

BRIEF DESCRIPTION OF THE DRAWINGS

Corresponding reference characters indicate corresponding parts throughout the several views of the drawings.

DETAILED DESCRIPTION OF THE PREFERRED EMBODIMENTS

The following description is presented to enable one of ordinary skill in the art to make and use the invention and is provided in the context of a patent application and its requirements. Various modifications to the preferred embodiments will be readily apparent to those skilled in the art and the generic principles herein may be applied to other embodiments. Thus, the present invention is not intended to be limited to the embodiment shown but is to be accorded the widest scope consistent with the principles and features described herein.

Figure 1:
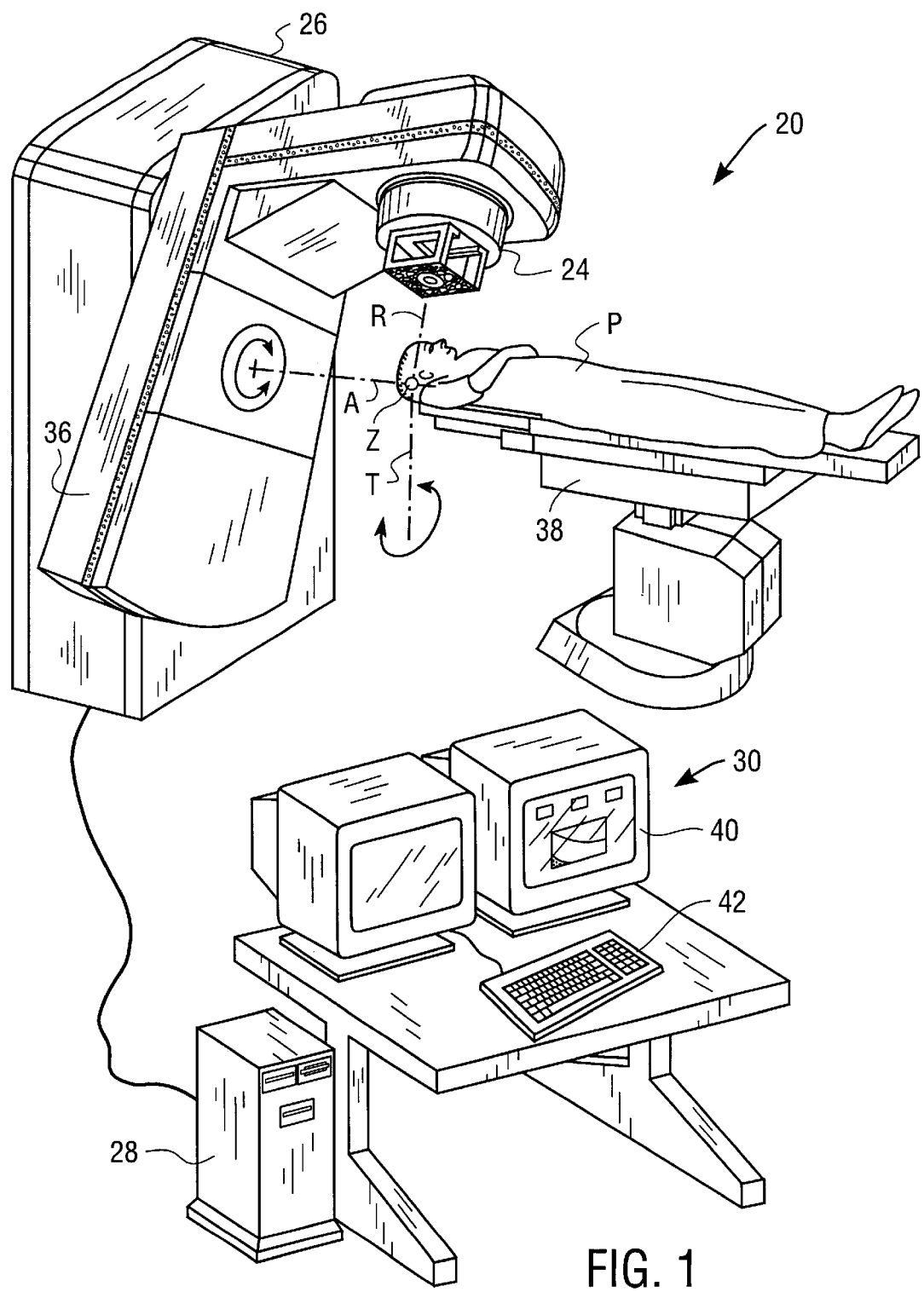
FIG. 1 is a diagram of a radiation treatment device and treatment console according to an embodiment of the present invention and a patient positioned for treatment within the treatment device.

Referring now to the drawings, and first to FIG. 1, a radiation treatment device of the present invention is shown and generally indicated at 20. The radiation treatment device 20 includes a beam shielding device (not shown) within a treatment head 24, a control unit within a housing 26 connected to a treatment processing unit, generally indicated at 30. The radiation treatment device further includes a gantry 36 which can be swiveled for rotation about axis A in the course of a therapeutic treatment. The treatment head 24 is fixed to the gantry 36 for movement therewith and a linear accelerator is located within the gantry for generating high powered radiation used for therapy. The radiation emitted from the linear accelerator extends generally along axis R. Electron, photon, or any other detectable radiation may be used for the therapy. During treatment, the radiation beam is focused on a zone Z of an object P (e.g., a patient who is to be treated). The zone to be treated is located at an isocenter defined by the intersection of the rotational axis A of the gantry 36, rotational axis T of treatment table 38, and the radiation beam axis R. The rotatable gantry 36 allows for different beam angles and radiation distributions without having to move the patient.

The treatment processing unit 30 is used to input information, such as radiation intensity and location of treatment, into the radiation treatment device 20 and output data for monitoring of the treatment. The processing unit 30 includes an output device such as a visual display monitor 40 and an input device such as a keyboard 42. The treatment processing unit 30 is typically operated by a therapist who administers actual delivery of radiation treatment as prescribed by an oncologist. The therapist uses the keyboard 42 to enter data, which defines the radiation dose to be delivered to the patient, into the processing unit 30. The data may also be input via other input devices, such as a data storage device, for example. Various types of data can be displayed before and during the treatment on the screen of the display monitor 40.

Figure 2:
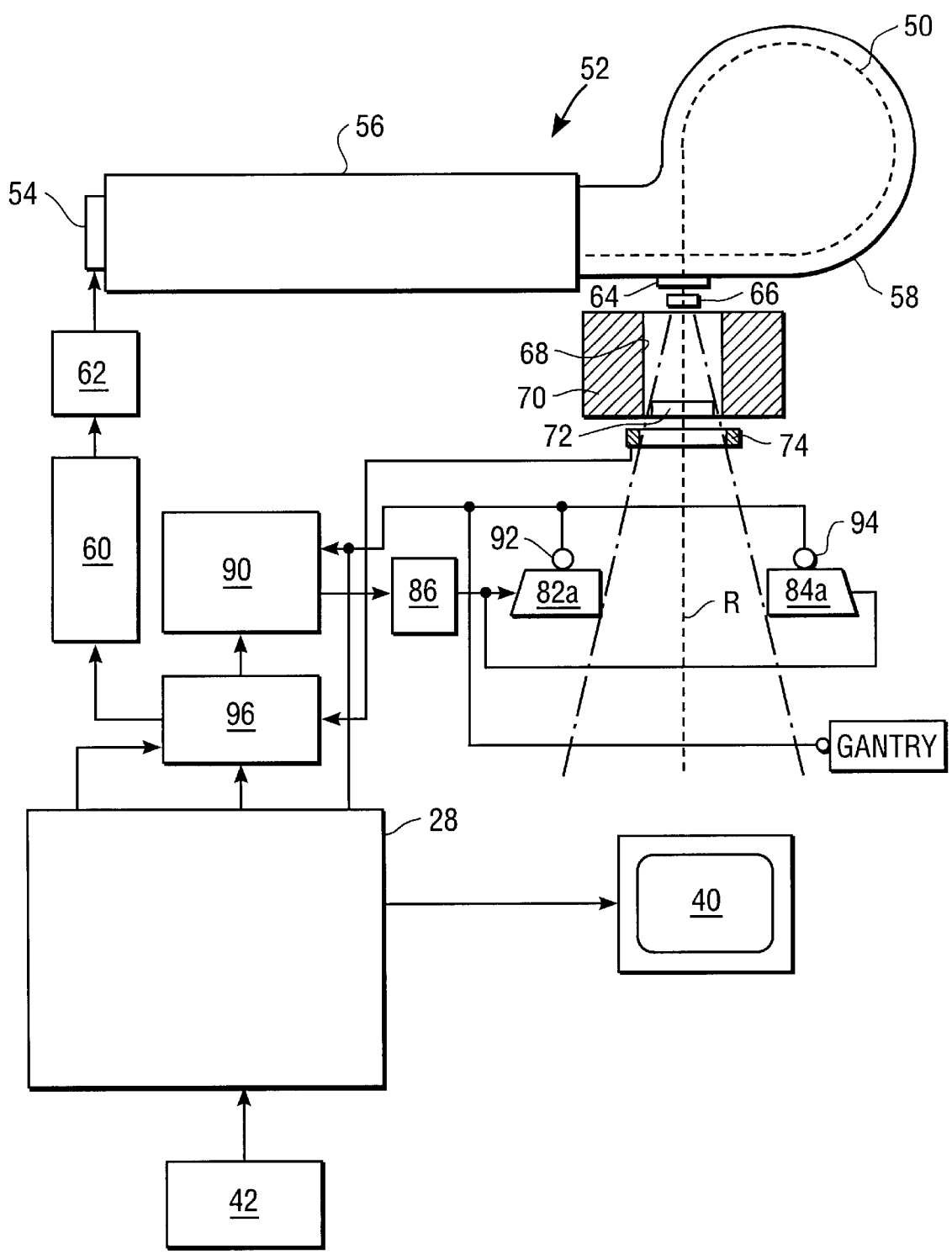
FIG. 2 is a block diagram illustrating portions of the radiation treatment device of FIG. 1.

FIG. 2 is a block diagram of the radiation treatment device 20 showing portions of the treatment processing unit 30 in further detail. An electron beam 50 is generated in an electron accelerator, generally indicated at 52. The electron accelerator 52 includes an electron gun 54, wave guide 56, and an evacuated envelope or guide magnet 58. A trigger system 60 generates injector trigger signals and supplies them to an injector 62. Based on these injector trigger signals, the injector 62 generates injector pulses which are fed to the electron gun 54 in the accelerator 52 for generating electron beam 50. The electron beam 50 is accelerated and guided by the wave guide 56. For this purpose, a high frequency source (not shown) is provided, which supplies radio frequency signals for the generation of an electromagnetic field supplied to the wave guide 56. The electrons injected by the injector 62 and emitted by the electron gun 54 are accelerated by the electromagnetic field in the wave guide 56 and exit at the end opposite the electron gun 54 to form electron beam 50. The electron beam 50 then enters the guide magnet 58 and from there is guided through a window 64 along axis R. After passing through a scattering foil 66 for electron mode (or target for photon mode), the beam 50 passes through a passageway 68 of a shield block 70 and encounters a secondary scattering foil 72 for electron mode (or flattening filter for photon mode). The beam next passes through a measuring chamber 74 in which the dose is ascertained.

Figure 3:
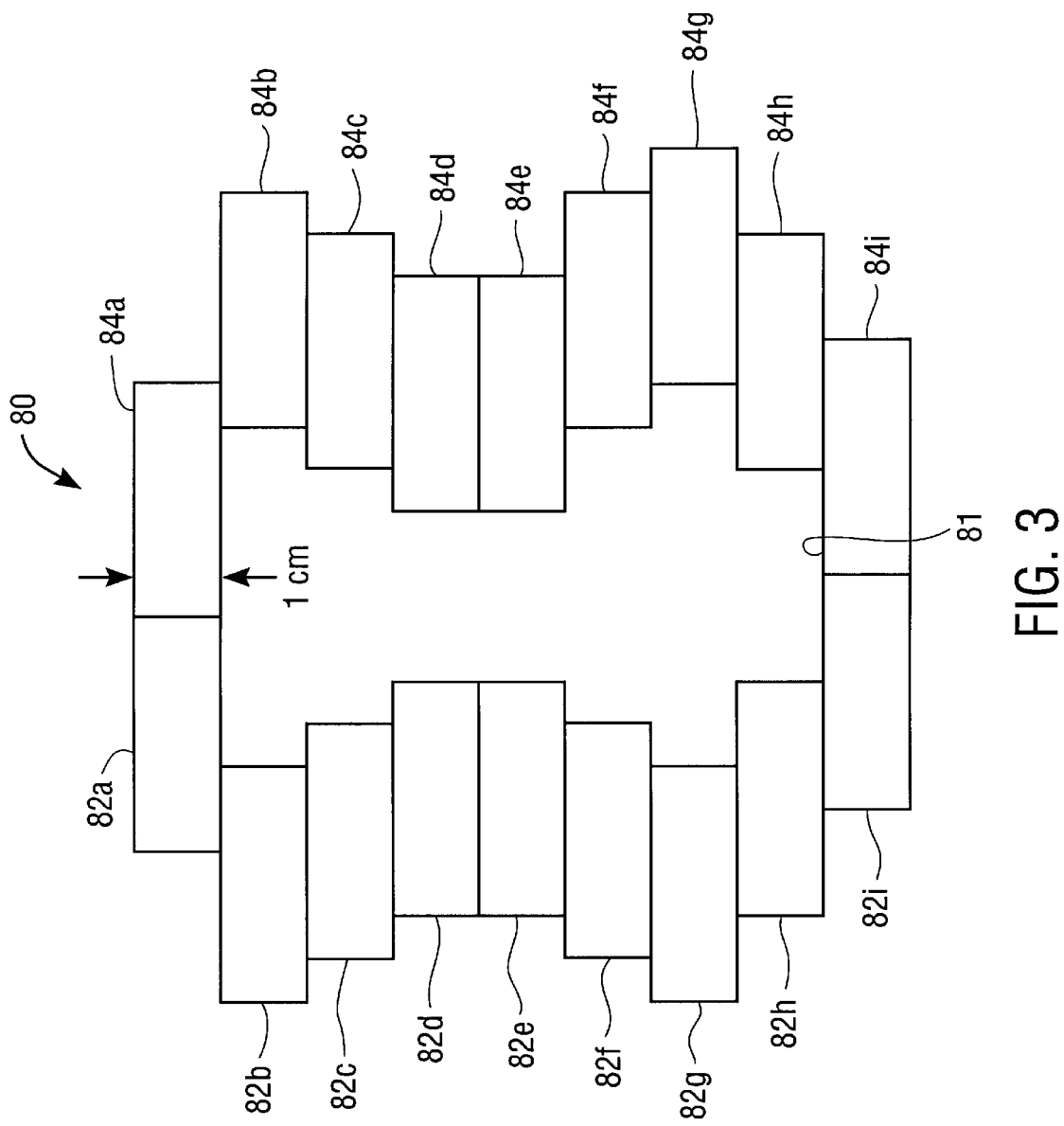
FIG. 3 is a schematic illustrating leaves of a multi-leaf collimator positioned for treatment in the radiation treatment device of FIG. 1.

A beam shielding device, generally indicated at 80, is provided in the path of the beam 50 to define a radiation field 81 (FIGS. 2 and 3). The beam shielding device 80 includes a plurality of opposing plates or leaves 82*a–i* and 84*a–i*, only two of which are shown in FIG. 2 for simplification. FIG. 3 illustrates leaves 82*a–i* and 84*a–i* (forming leaf pairs 82*a* and 84*a*, 82*b* and 84*b*, . . . , 82*i* and 84*i*) of a multi-leaf collimator mounted between the radiation source and patient and positioned to define a treatment field by delimiting the electron beam 50. The leaves 82*a–i*, 84*a–i* typically have a one centimeter width and are substantially impervious to the emitted radiation so that they block healthy tissue from the radiation.

The leaves 82*a–i*, 84*a–i* are movable in a direction generally perpendicular to axis R by a drive unit 86 (which is shown in FIG. 2 only with respect to plate 82*a*) to change the size of the irradiated field so that the distribution of radiation over the field does not need to be uniform (i.e., one region may be exposed to a higher dose than another region). The drive unit 86 includes an electric motor which is coupled to the plate 82*a* and controlled by a motor controller 90. Position sensors 92, 94 are also coupled to plates 82*a*, 84*a*, respectively, for sensing their positions. The drive unit 86 drives the plate 82*a* in and out of the treatment field, thus creating the desired field shapes.

The motor controller 90 is coupled to a dose control unit 96 which includes a dosimetry controller coupled to the central processing unit 28 for providing set values for the radiation beam for achieving given isodose curves (FIG. 2). The output of the radiation beam is measured by the measuring chamber 74. In response to the deviation between the set values and the actual values, the dose control unit 96 supplies signals to the trigger system 60 which change in a known manner the pulse repetition frequency so that the deviation between the set values and the actual values of the radiation beam output is minimized. The dose absorbed by the patient is dependent upon movement of the collimator plates 82a, 84a. The central processing unit 28 controls execution of the program and the opening and closing of the collimator plates 82a, 84a to deliver radiation according to a desired intensity profile. The central processing unit 28 may include other features described in U.S. Pat. No. 5,724,403, which is incorporated herein by reference in its entirety, for example.

It is to be understood that the radiation treatment device may be different than the one described and shown herein without departing from the scope of the invention. The treatment device 20 described above is provided as an example of a device for use in delivering a treatment developed by the optimization process described below.

Figure 4:
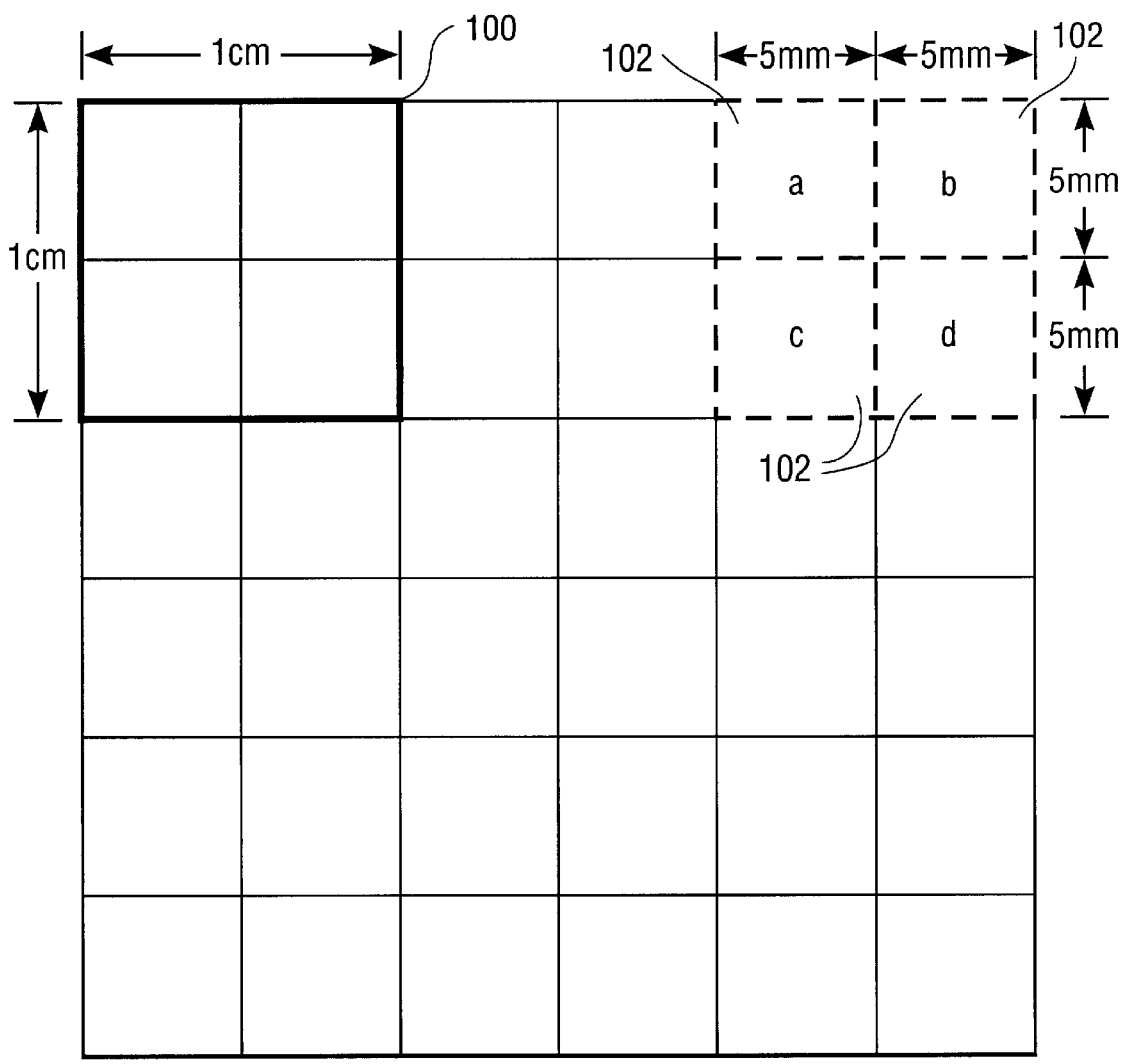
FIG. 4 is a schematic illustrating cells located in an intensity map.

FIG. 4 illustrates an intensity map having a plurality of 1 cm×1 cm macrocells 100 (indicated by dark lines) divided into four 5 mm×5 mm microcells 102 (indicated by dashed lines). The 5 mm×5 mm in microcells 102 are used to convert macrocell 100 into two orthogonal intensity maps, one with a resolution of 5 mm×10 mm, and the other with a resolution of 10 mm×5 mm. An example of a process for dividing the intensity map into groups of four 5 mm×5 mm microcells 102 is described in U.S. patent application Ser. No. 09/234,364, by A. Siochi, filed Jan. 20, 1999, which is incorporated herein by reference in its entirety. This grouping of 5 mm×5 mm microcells 102 allows for treatment of a field with a 5 mm×5 mm resolution using a multi-leaf collimator having one centimeter leaves, as shown in FIG. 3.

Figure 5:
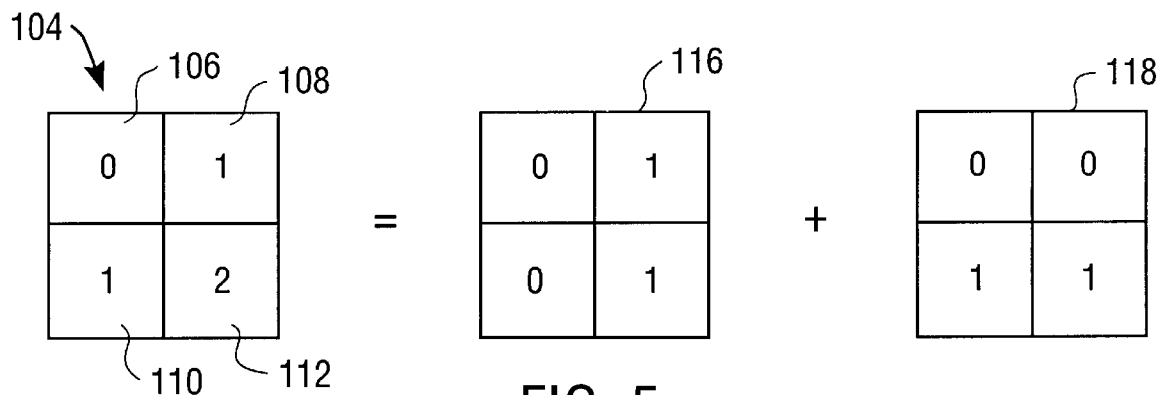
FIG. 5 is a diagram of a matrix broken down into a zero degree matrix component and a ninety degree matrix component.
Figure 6:
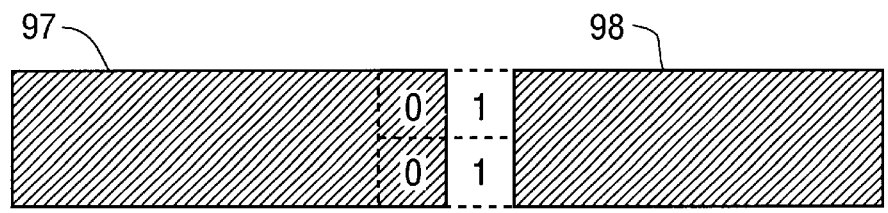
FIG. 6 is a plan view of an opposing pair of leaves configured to apply a dosage specified by the zero degree matrix of FIG. 5.
Figure 7:
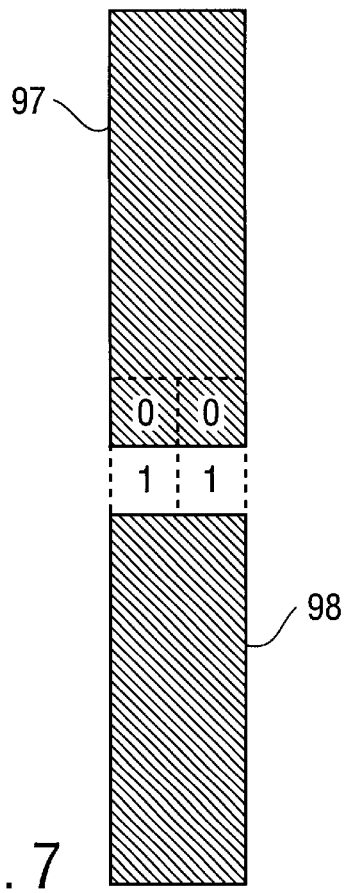
FIG. 7 is a plan view of an opposing pair of leaves configured to apply a dosage specified by the ninety degree matrix of FIG. 5.

FIG. 5 illustrates an example of a matrix, generally indicated at 104 formed from an intensity map composed of four 5 mm×5 mm microcells 106, 108, 110, 112. Each microcell 106, 108, 110, 112 identifies a section in a field to be treated with radiation. The numbers (0, 1, 1, 2) within each microcell 106, 108, 110, 112, respectively, represent the radiation intensity level for locations within the field and are in monitor units (mu) or relative monitor unit intensities (e.g., $1 \times 10^2$ mu). In order to provide 5 mm×5 mm resolution for the intensity map, the matrix 104 is broken down into two orthogonal matrices, 116, 118 having a 1 cm×5 mm resolution and 5 mm×1 cm resolution, respectively. A one centimeter leaf width multi-leaf collimator may then be used to deliver the intensity map with a 5 mm×5 mm resolution. For example, a pair of leaves 97, 98 positioned as shown in FIG. 6 may be used to deliver the map intensity shown in matrix 116 of FIG. 5. A dose of radiation (e.g., 1 mu) is applied to fields corresponding to microcells 108 and 112 of matrix 104. The collimator is then rotated approximately ninety degrees to deliver the map intensity shown in matrix 118 with the leaf position shown in FIG. 7. With the collimator rotated ninety degrees, a dose of radiation (e.g., 1 mu) is applied to the fields corresponding to microcells 110 and 112 of matrix 104. The two radiation applications result in a 2 mu dose to the field corresponding to microcell 112, a 1 mu dose to the fields corresponding to microcells 108 and 110, and no radiation being applied to the field corresponding to microcell 106. The decomposition of the matrix 104 into orthogonal matrices 116 and 118 thus provides for 5 mm×5 mm resolution treatment using collimator leaves having a one centimeter width.

In the following description, the original input intensity map is defined as a macromatrix and the groups of four microcells within the macromatrix are defined as microma-trices (or matrices). In order for the intensity map to be decomposed into orthogonal maps, the vertical gradients of each column of the micromatrix (matrix) 100 must be equal to one another and the horizontal gradients of each row of the micromatrix must also be equal to one another (FIG. 4). This provides a 1 cm×1 cm area under the intersection of one leaf pair for one collimator setting and another leaf pair for the orthogonal collimator setting. For example, if the horizontal gradients are equal for the micromatrix having cells 102 (shown in FIG. 4) the following equation must apply:

$$b-a=d-c;$$

where: a, b, c, d are the intensity values corresponding to locations in the micromatrix 100 of FIG. 4

Similarly, if the vertical gradients are equal the following equation must apply:

$$c-a=d-b.$$

The following describes a method for converting an intensity map which does not meet the above constraints (i.e., horizontal gradients for each row are not equal or vertical gradients for each column are not equal), into an intensity map having equal horizontal gradients and equal vertical gradients. Preferably, the average value of the intensity of the four cells and their average horizontal and vertical gradients are maintained during the conversion, as further described below. Once the intensity map is converted, the map may be decomposed as described in U.S. patent application Ser. No. 09/457,602 by A. Siochi, filed Dec. 2, 1999 (incorporated by reference herein in its entirety) and an optimization method described therein may be used to find a decomposition which will yield the shortest treatment delivery time.

Figure 8:
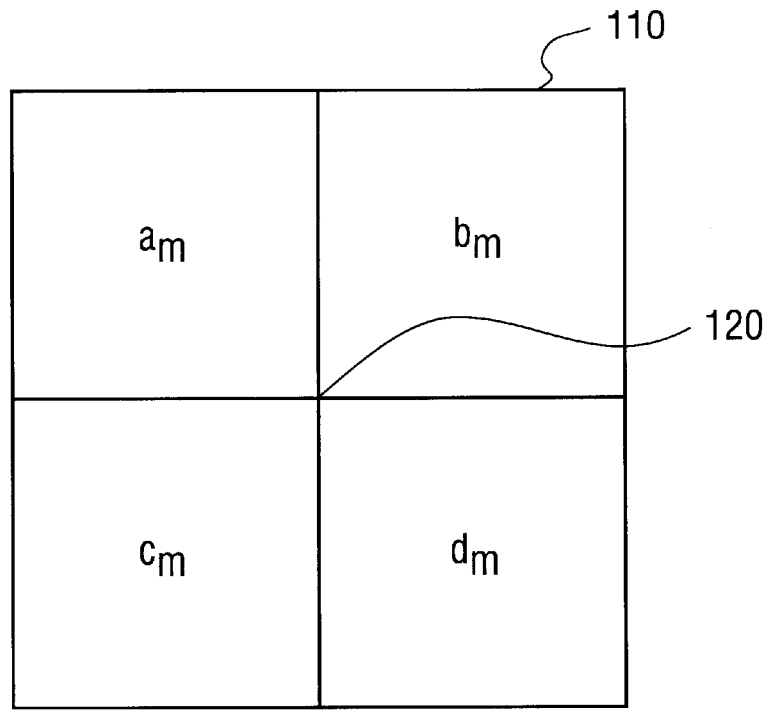
FIG. 8 illustrates a micromatrix prior to filtering of the cell intensity values.
Figure 9:
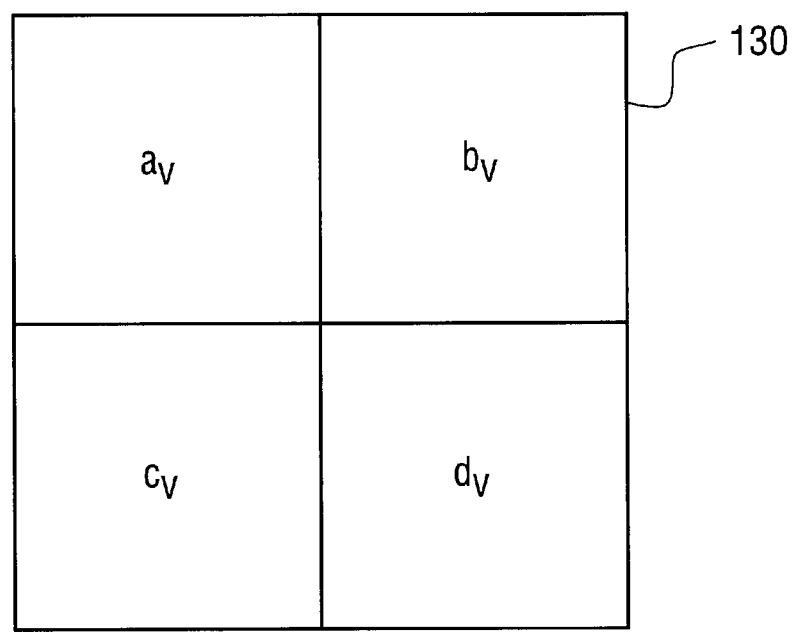
FIG. 9 illustrates the micromatrix of FIG. 8 after filtering of the cell intensity values.

FIG. 8 illustrates an exemplary mapping 110 of microcells $a_m$, $b_m$, $c_m$, and $d_m$. An average horizontal gradient for micromatrix 110 is defined as follows:

$$\Delta H = ((b_m - a_m) + (d_m - c_m))/2$$

An average vertical gradient for the micromatrix 110 is defined as:

$$\Delta V = ((c_m - a_m) + (d_m - b_m))/2$$

An average intensity value for the micromatrix 110 is defined as:

$$M = (a_m + b_m + c_m + d_m)/4$$

The horizontal gradient $\Delta H$ and vertical gradient $\Delta V$ defined above, provide the average intensity level for the rows and columns, respectively, of micromatrix 110. The average intensity value M defines the average cell intensity value over the entire micromatrix 110. The average horizontal and vertical gradients are preferably preserved during conversion of the micromatrix 110. The new intensity values are defined by having the average intensity value occur generally at a location common to all cells (i.e., point 120). The cell intensity values are then found by treating the horizontal and vertical gradients as vectors and moving in half steps of some combination of the vertical and horizontal gradients, as further described below. There may be a requirement that all cell intensity values are integers, due to the optimization method used on the converted intensity values, or the treatment device used to deliver the intensity map, for example. The equations set forth below are provided first for the case where there is no restriction on the cell intensity values (i.e., values may be fractions), and then provided for the case where the intensity values must be integers.

The following equations are used to convert the intensity values from the original micromatrix 110 to a transformed micromatrix 130 (with no constraint on the discreteness of intensity values):

$$a_v = M - \Delta V/2 - \Delta H/2$$

$$b_v = a_v + \Delta H$$

$$c_v = a_v + \Delta V$$

$$d_v = c_v + \Delta H$$

where: $a_v$, $b_v$, $c_v$, and $d_v$ are the converted intensity values corresponding to $a_m$, $b_m$, $c_m$, and $d_m$ of the original micromatrix 110.

If there is a constraint on the discreteness of the intensity values (i.e., they can only be represented as integers) then the following equations are used:

$$a_v = \text{round}(M - \Delta V/2 - \Delta H/2)$$

$$b_v = a_v + \text{round}(\Delta H)$$

$$c_v = a_v + \text{round}(\Delta V)$$

$$d_v = c_v + \text{round}(\Delta H)$$

The round function rounds the value in parenthesis either up or down to the next closest integer. For example if the value is 4.2 it will be rounded to 4, if the value is 4.8 it will be rounded to 5.

The calculation of $a_v$, $b_v$, $c_v$, and $d_v$ may result in some values being negative (i.e., less than 0). A minimum value N of the intensity values of micromatrix 130 is defined as:

$$N = \text{Min}(a_v, b_v, c_v, d_v)$$

If N is less than zero, the cell intensity values of the micromatrix 130 will need to be adjusted so that the values are all positive. The following provides three examples of methods which may be used to adjust the intensity values of the cells so that all of the cells within micromatrix 130 have a positive intensity value.

The first method maintains the horizontal and vertical gradients $\Delta H$, $\Delta V$ while raising the average intensity value M. A minimum value N (defined above) is subtracted from the intensity value of each cell:

$$a'_v = a_v - N$$

$$b'_v = b_v - N$$

$$c'_v = c_v - N$$

$$d'_v = d_v - N$$

For example, if the transformed matrix 130 has intensity values of $a_v = -1$, $b_v = 1$, $c_v = 2$, and $d_v = 4$, the minimum value N is equal to −1 (the intensity value of cell $a_v$). Since N is less than zero the values of the cells need to be adjusted so that every cell is positive. The above equations may be applied to adjust the values as follows:

$$a'_v = (^{-}1) - (-1) = 0$$

$$b'_v = 1 - (^{-}1) = 2$$

$$c'_v = 2 - (^{-}1) = 3$$

$$d'_v = 4 - (^{-}1) = 5$$

A second process, which may be used to adjust the cell values so that they are all positive, maintains the maximum intensity value of the micromatrix 130, raises the average value M, and reduces the average horizontal and vertical gradients $\Delta H$, $\Delta V$. A variable P which represents the maximum intensity value of the micromatrix 130 is defined as follows:

$$P = \text{Max}(a_v, b_v, c_v, d_v)$$

A new average cell value M' is calculated as:

$$M' = P/2$$

The average horizontal and vertical gradients are also recalculated as follows:

$$\Delta H' = \Delta H * P / (P - N)$$

$$\Delta V' = \Delta V * P / (P - N)$$

If there is no constraint on the discreteness of the intensity value, the following equations apply:

$$a'_v = M' - \Delta V'/2 - \Delta H'/2$$

$$b'_v = a_v + \Delta H'$$

$$c'_v = a_v + \Delta V'$$

$$d'_v = c_v + \Delta H'$$

If there is a constraint on the discreteness of the intensity values (i.e., they can only be represented as integers) then the following equations are used:

$$a'_v = \text{roundup}(M' - \Delta V'/2 - \Delta H'/2)$$

$$b'_v = a'_v + \text{roundup}(\Delta H')$$

$$c'_v = a'_v + \text{roundup}(\Delta V')$$

$$d'_v = c'_v + \text{roundup}(\Delta H')$$

For this process the roundup function rounds the values up to the more positive integer. For example, if the value is 4.2 it will be rounded up to 5.

The following example uses the second process to adjust the values of matrix 130 having intensity values $a_v = ^{-}1$, $b_v = 1$, $c_v = 2$ and, $d_v = 4$. The average horizontal and vertical gradients $\Delta H$, $\Delta V$ and the average intensity value M of the micromatrix are calculated as:

$$\Delta H = ((1 - (^{-}1)) + (4 - 2))/2 = 2$$

$$\Delta V = ((2 - (^{-}1)) + (4 - 1))/2 = 3$$

$$M = ((^{-}1) + 1 + 2 + 4)/4 = 1.5$$

It should be noted that $\Delta H$, $\Delta V$, and M can be calculated from the first converted micrormatrix 130, since these values are the same for both the original micromatrix 110 and the converted micromatrix 130. The maximum value P is equal to 4 ($d_v$) and the minimum value N is equal to −1($a_v$). The new average cell intensity value M' can then be calculated:

$$M' = 4/2 = 2$$

The new average horizontal and vertical gradients $\Delta H'$, $\Delta V'$ are also calculated:

$$\Delta H' = 2 * 4 / (4 - (^{-}1)) = 8/5$$

$$\Delta V' = 3 * 4 / (4 - (^{-}1)) = 12/5$$

If there is no constraint on the discreteness of the intensity values, the new intensity values are calculated as follows:

$a'_v = 2 - (12/5)/2 - (8/5)/2 = 0$ $b'_v = 0 + 8/5 = 8/5$ $c'_v = 0 + 12/5 = 12/5$ $d'_v = 12/5 + 8/5 = 4$

If there is a constraint on the discreteness of the intensity value (i.e., intensity value must be an integer), the new intensity values are calculated as follows:

$a'_v = 0$ $b'_v = 0 + 2 = 2$ $c'_v = 0 + 3 = 3$ $d'_v = 3 + 2 = 5$

A third process, which may be used to adjust the cell values so that they are all positive, maintains the average cell intensity value M, and reduces the average horizontal and vertical gradients. The new average horizontal and vertical gradients are calculated as follows:

$\Delta H'' = \Delta H * 2 * M/(P-N)$ $\Delta V'' = \Delta V * 2 * M/(P-N)$

If there is no constraint on the discreteness of the intensity values, the following equations are used:

$a'_v = M - \Delta V''/2 - \Delta H''/2$ $b'_v = a'_v + \Delta H''$ $c'_v = a'_v + \Delta V''$ $d'_v = c'_v + \Delta H''$ If there is a constraint on the discreteness of the intensity values, the following equations are then used:

$a'_v = \text{roundup}(M - \Delta V''/2 - \Delta H''/2)$ $b'_v = a'_v + \text{roundup}(\Delta H'')$ $c'_v = a'_v + \text{roundup}(\Delta V'')$ $d'_v = c'_v + \text{roundup}(\Delta H'')$ The roundup function is the same as described above where the values are rounded up to the more positive integer. This is done to avoid having negative numbers in the final matrix.

The following example for the third process uses the same values for the micromatrix 130 ($a_v = ^-1$, $b_v = 1$, $c_v = 2$, $d_v = 4$). As described above, M=1.5 N=$^-$1, and P=4. The new horizontal and vertical gradients are first calculated:

$\Delta H'' = 2 * 2 * 1.5/(4-(^-1)) = 6/5$ $\Delta V'' = 3 * 2 * 1.5/(4-(^-1)) = 9/5$ If there is no constraint on the discreteness of the intensity value, the intensity values are calculated as follows:

$a'_v = 1.5 - (9/5)/2 - (6/5)/2 = 0$ $b'_v = 0 + 6/5 = 6/5$ $c'_v = 0 + 9/5 = 9/5$ $d'_v = 9/5 + 6/5 = 3$

If the intensity value must be an integer, the values are then calculated as follows:

$a'_v = 0$ $b'_v = 0 + 2 = 2$ $c'_v = 0 + 2 = 2$ $d'_v = 2 + 2 = 4$

Figure 10:
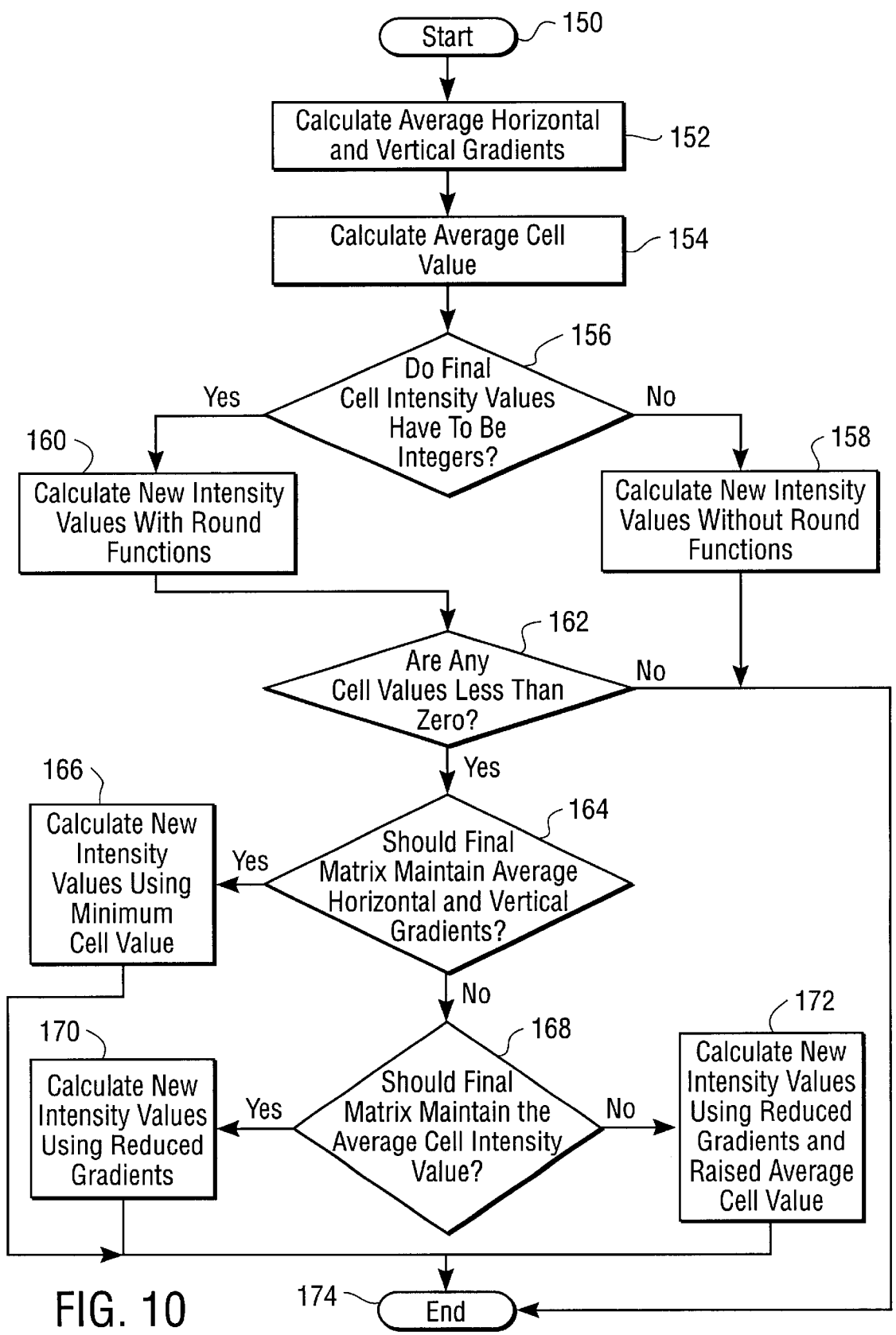
FIG. 10 is a flowchart illustrating a process for filtering the micromatrix.

FIG. 10 is flowchart illustrating a process for converting the micromatrix 110 into micromatrix 130, which has the horizontal gradients of each row equal to one another and the vertical gradients of each column equal to one another. The process is started at step 150 and begins with the calculation of the average horizontal and vertical gradients (step 152) and the average cell value (step 154). If the cell intensity values do not have to be integers, the average horizontal gradient, average vertical gradient, and average cell value are used to calculate the final cell intensity values (steps 156, 158). If there is a requirement that the final cell intensity values have to be integers, the intensity values are calculated using the round functions, as described above (steps 156 and 160). If all the cell values are greater than zero the process is ended (steps 162 and 174). If any of the cell intensity values is less than zero one of three processes are used to convert the intensity values into positive values. If it is desired to maintain the average horizontal and vertical gradients, the new intensity values are calculated using the minimum cell value to transform the cell values to positive values (steps 164, 166, and 174). If it is desired to maintain the average cell intensity value of the micromatrix, the new intensity values are calculated using reduced horizontal and vertical gradients (steps 168 and 170). If there is not a requirement to maintain the average cell intensity value of the micromatrix, the new intensity values are calculated using reduced horizontal and vertical gradients and a raised average cell value (steps 168 and 172). If the process of steps 170 or 172 is used, round functions have to be used if the final cell values are required to be integers (steps 156 and 160). Since the process of step 166 only subtracts the minimum value from all of the intensity values, if the values are initially integers they will remain integers. Thus, round functions do not need to be applied to the process of step 166. The processes of steps 170 and 172, however, may create non-integer values even if integer values are used.

The specific process which is used to convert negative cell values into positive values depends on the area to be treated, or the type of treatment being given to a patient. The first process may be used, for example, in defining an intensity map for radiation treatment on a prostate tumor which is typically tolerable to high doses of radiation. The second process may be used, for example, for a tumor located in the head or neck area since these areas can not tolerate higher doses of radiation, and gradient values are more important. The third process is safest to use if the specific anatomy location of the tumor is not known, since the average cell value is maintained.

The above example uses an intensity map represented by a 2×2 matrix, however, the intensity map may have a size different than shown herein and may be mapped using various size matrices. Also, a multi-leaf collimator having leaves with a width other than 1 cm may be used, and the size of the corresponding microcells will be 1/n times the leaf width (where n is a positive integer (e.g., 2 or 3)). The intensity map may be broken down into microcells having a dimension other than 5 mm×5 mm if a different resolution is required. For example, each macrocell may be divided into nine microcells in which case the intensity map may be deliverable as two orthogonal intensity maps having a resolution of 1 cm×1/3 cm and 1/3 cm×1 cm (see, for example, U.S. patent application Ser. No. 09/234,364, referenced above). If the macrocell is divided into nine microcells, the macrocell would be modified by the filter such that the vertical gradients in pairs of adjacent rows are equal, and the horizontal gradient in pairs of adjacent columns are equal. For example, the first two rows of the macrocell will be grouped to form a 2×3 matrix (i.e., two rows×three columns) which will be modified such that the vertical gradients in each of the columns are equal. A second 2×3 matrix is then formed with the second and third rows of the macrocell and modified such that the vertical gradients in each of the columns are equal. The first two columns of the macrocell will then be grouped to form a 3×2 matrix (i.e., three rows×two columns) which will be modified such that the horizontal gradients in each row are equal to one another. The same is then done for the second and third columns. In order to retain the gradients for the for the first and second rows or first and second columns, the intensity values for the cells in the third row or third column will be modified, while maintaining the intensity values of the cells in the rows or columns which have already been modified.

Once the pairs of rows and columns are formed, the new cell intensity values are calculated by treating the horizontal and vertical gradients as vectors and moving in half steps of some combination of the vertical and horizontal gradients, as described above. The equations used above for the 2×2 matrix will be modified for use on the specific size matrix (e.g., 2×n or n×2; where n is a positive integer).

An average value may also be defined for the entire matrix, and the new cell intensity values calculated by moving from the center point of the matrix to the other cell locations with some combination of the average horizontal and vertical gradients. In this process, the equations for the 2×2 matrix are extended to the entire 3×3 matrix. For example, for a 3×3 matrix, two average vertical gradients (one from the first row to the second row v(1,2) and one from the second row to the third row v(2,3)) are defined. Similarly, two average horizontal gradients are defined (one from the first column to the second column h(1,2) and one from the second column to the third column h(2,3)). An average value M of the entire matrix (sum of cells divided by nine) corresponds to the center of the matrix (cell (2,2)). The values for the remaining cells are calculated by adding or subtracting the appropriate average horizontal and vertical gradients. For example, the value for cell (1,2) is equal to M minus v(1,2), and the value for cell (1,1) is equal to M minus h(1,2) and v(1,2). Similarly, the value for cell (1,3) is equal to M plus v(2,3) and minus h(1,2). This process may be performed on matrices having sizes other than 3×3.

Although the present invention has been described in accordance with the embodiments shown, one of ordinary skill in the art will readily recognize that there could be variations to the embodiment and these variations would be within the spirit and scope of the present invention. Accordingly, many modifications may be made by one of ordinary skill in the art without departing from the spirit and scope of the appended claims.

What is claimed is:

1. A method for defining an intensity map for use in delivering radiation from a radiation source to an object with a multi-leaf collimator, the method comprising:
   defining a field on the object for radiation delivery, said field including a plurality of cells each having a defined treatment intensity level;
   grouping at least a portion of the cells to form a matrix; and
   modifying the treatment intensity level of the cells within the matrix such that horizontal gradients of pairs of rows of the matrix are equal to one another and vertical gradients of pairs of columns of the matrix are equal to one another.

2. The method of claim 1 further comprising delivering radiation with a resolution higher than a leaf width of the multi-leaf collimator.

3. The method of claim 2 wherein the resolution is one half the leaf width.

4. The method of claim 1 wherein modifying the treatment intensity level comprises modifying the intensity level such that the intensity level is an integer.

5. The method of claim 1 wherein grouping at least a portion of the cells comprises grouping four cells.

6. The method of claim 1 wherein grouping at least a portion of the cells comprises grouping nine cells.

7. The method of claim 6 wherein modifying the treatment intensity level of the cells comprises grouping two adjacent rows of the matrix to form one of the pairs of rows and two adjacent columns of the matrix to form one of the pairs of columns.

8. The method of claim 1 wherein modifying the treatment intensity level comprises calculating an average horizontal gradient for each pair of adjacent columns and an average vertical gradient for each pair of adjacent rows.

9. The method of claim 8 wherein modifying the treatment intensity level further comprises calculating an average matrix intensity value for each pair of rows and each pair of columns.

10. The method of claim 8 wherein modifying the treatment intensity level further comprises calculating an average matrix intensity value for the entire matrix.

11. The method of claim 8 wherein modifying the treatment intensity level includes applying the following equations:

$$a_v = M - \Delta V/2 - \Delta H/2$$

$$b_v = a_v + \Delta H$$

$$c_v = a_v + \Delta V$$

$$d_v = c_v + \Delta H$$

where: $a_v$, $b_v$, $c_v$, and $d_v$ are modified intensity levels;
M=the average matrix intensity value;
$\Delta H$=the average horizontal gradient; and
$\Delta V$=the average vertical gradient.

12. The method of claim 8 further comprising modifying the treatment intensity level of the cells within the matrix such that all intensity levels are greater than zero.

13. The method of claim 12 wherein modifying the treatment intensity level further comprises maintaining the average horizontal and vertical gradients and raising the average matrix intensity value.

14. The method of claim 12 wherein modifying the treatment intensity level further comprises maintaining a maximum matrix intensity value, raising the average matrix intensity value, and reducing the average horizontal and vertical gradients.

15. The method of claim 12 wherein modifying the treatment intensity level further comprises maintaining the average matrix intensity value and reducing the average horizontal and vertical gradients.

16. A system for defining an intensity map for use in delivering radiation from a radiation source to an object having a field defined thereon for radiation delivery, said field including a plurality of cells having predefined treatment intensity levels, the system comprising:

a processor for receiving the cells, grouping at least a portion of the cells to form a matrix, and modifying the treatment intensity level of the cells within the matrix such that horizontal gradients of pairs of rows of the matrix are equal to one another and vertical gradients of pairs of columns of the matrix are equal to one another.

17. The system of claim 16 further comprising a collimator having multiple leaves for blocking radiation from said source and defining an opening between the radiation source and said object.

18. The system of claim 17 wherein the matrix has at least one dimension approximately equal to a width of one of the collimator leaves.

19. The system of claim 18 wherein the collimator is operable to provide radiation treatment with a resolution approximately one half of the width of the leaves.

20. The system of claim 19 wherein the matrix comprises four cells.

21. The system of claim 16 wherein the processor is operable to modify the intensity levels of the cells such that the intensity levels are integers.

22. The system of claim 16 wherein the processor is operable to calculate an average horizontal gradient, an average vertical gradient, and an average matrix intensity value.

23. The system of claim 22 wherein the processor is operable to modify the treatment intensity level of the cells within the matrix such that all intensity levels are greater than zero.

* * * * *